US011761916B2

United States Patent
Choa et al.

(10) Patent No.: US 11,761,916 B2
(45) Date of Patent: Sep. 19, 2023

(54) GAS SENSOR AND METHOD FOR MANUFACTURING SAME

(71) Applicant: INDUSTRY-UNIVERSITY COOPERATION FOUNDATION HANYANG UNIVERSITY ERICA CAMPUS, Ansan-si (KR)

(72) Inventors: Yong Ho Choa, Ansan-si (KR); Seil Kim, Ansan-si (KR); Yoseb Song, Ansan-si (KR)

(73) Assignee: INDUSTRY-UNIVERSITY COOPERATION FOUNDATION HANYANG UNIVERSITY ERICA CAMPUS, Ansan-si (KR)

(*) Notice: Subject to any disclaimer, the term of this patent is extended or adjusted under 35 U.S.C. 154(b) by 600 days.

(21) Appl. No.: 16/538,739

(22) Filed: Aug. 12, 2019

(65) Prior Publication Data

US 2019/0360955 A1   Nov. 28, 2019

Related U.S. Application Data

(63) Continuation of application No. PCT/KR2018/000537, filed on Jan. 11, 2018.

(30) Foreign Application Priority Data

Mar. 22, 2017   (KR) .................. 10-2017-0035810

(51) Int. Cl.
*G01N 25/32*   (2006.01)
*G01N 1/22*   (2006.01)
(Continued)

(52) U.S. Cl.
CPC .......... *G01N 25/32* (2013.01); *G01N 1/2273* (2013.01); *H10N 10/01* (2023.02); *H10N 10/857* (2023.02); *G01N 31/10* (2013.01)

(58) Field of Classification Search
CPC ...... G01N 25/32; G01N 1/2273; G01N 31/10; H01L 35/26; H01L 35/34
See application file for complete search history.

(56) References Cited

U.S. PATENT DOCUMENTS 9,133,549 B2   9/2015  Kim et al.
2017/0110643 A1*  4/2017  Choa .................. H01L 35/34

FOREIGN PATENT DOCUMENTS

JP   2009133636 A   6/2009
JP   2010-122106 A   6/2010
(Continued)

OTHER PUBLICATIONS

Kim, Seil, et al. "Thermochemical hydrogen sensor based on chalcogenide nanowire arrays." Nanotechnology 26.14 (2015): 145503. (Year: 2015).*

(Continued)

*Primary Examiner* — Robert J Eom
(74) *Attorney, Agent, or Firm* — Studebaker & Brackett PC

(57) ABSTRACT

A method for manufacturing a gas sensor may be provided, the method comprising the steps of: preparing a metal nanowire; manufacturing a thermoelectric composite by adding a polymer bead to the metal nanowire, and then mechanically mixing same; manufacturing a thermoelectric layer by hot-pressing the thermoelectric composite; forming a first electrode on the upper surface of the thermoelectric layer, and forming a second electrode on the lower surface of the thermoelectric layer; and disposing a heating catalyst layer on the first electrode.

10 Claims, 10 Drawing Sheets

(51) Int. Cl.
  *H10N 10/01*  (2023.01)
  *H10N 10/857*  (2023.01)
  *G01N 31/10*  (2006.01)

(56) References Cited

FOREIGN PATENT DOCUMENTS

| KR | 10-2006-0122576 A | 11/2006 |
|---|---|---|
| KR | 10-1067557 B1 | 9/2011 |
| KR | 10-2014-0106812 A | 9/2014 |
| KR | 10-2015-0142984 A | 12/2015 |
| KR | 10-2016-0040884 A | 4/2016 |
| KR | 1020160037149 A | 4/2016 |

OTHER PUBLICATIONS

Slobodian, Petr, et al. "Analysis of sensing properties of thermoelectric vapor sensor made of carbon nanotubes/ethylene-octene copolymer composites." Carbon 110 (2016): 257-266. (Year: 2016).*
Pandey, P. A., N. R. Wilson, and J. A. Covington. "Pd-doped reduced graphene oxide sensing films for H2 detection." Sensors and Actuators B: Chemical 183 (2013): 478-487. (Year: 2013).*
Kim, Seil, et al. "Synthesis and thermoelectric characterization of high density Ag2Te nanowire/PMMA nanocomposites." Materials Chemistry and Physics 190 (2017): 187-193. (Year: 2017).*
Pang, Huan, et al. "Conductive polymer composites with segregated structures." Progress in Polymer Science 39.11 (2014): 1908-1933. (Year: 2014).*
International Search Report issued in PCT/KR2018/000537; dated May 14, 2018.

\* cited by examiner

GAS SENSOR AND METHOD FOR MANUFACTURING SAME

CROSS-REFERENCE TO RELATED APPLICATIONS

The present application is a continuation of International Patent Application No. PCT/KR2018/000537, filed Jan. 11, 2018, which is based upon and claims the benefit of priority to Korean Patent Application No. 10-2017-0035810, filed on Mar. 22, 2017. The disclosures of the above-listed applications are hereby incorporated by reference herein in their entirety.

TECHNICAL FIELD

The present invention relates to a gas sensor and a method for manufacturing the same, and more particularly, to a gas sensor which includes a thermoelectric layer including a polymer bead on which metal nanowires are adsorbed and has excellent detectability and stability due to high electromotive force characteristics due to an exothermic catalyst layer on the thermoelectric layer, and a method for manufacturing the same.

BACKGROUND ART

Concerns about environmental pollution and depletion of fossil energy have raised interest in hydrogen energy as a low-pollution alternative energy source.

However, when being combined with oxygen in the atmosphere, hydrogen is spontaneously ignited or is exploded. Thus, a technology which can detect leakage of the hydrogen during production, storage, and use of the hydrogen is recognized as important.

Currently, hydrogen sensors, such as a semiconductor type hydrogen sensor, a field effect transistor (FET) type hydrogen sensor, an electrolytic type (electrochemical type) hydrogen sensor, an optical fiber type hydrogen sensor, a piezoelectric type hydrogen sensor, and a thermoelectric type hydrogen sensor, have been actively researched and developed.

In particular, in order to commercialize the hydrogen sensor, a measurement concentration range of the sensor, a short response time, precision, sensitivity, stability, miniaturization of the sensor, simplification of a process, and the like have been recognized as important.

For example, Korean Patent No. KR1067557B1 (Korean Patent Application No. KR20090132402A, Applicant: Industry-Academic Cooperation of Yonsei University) discloses a technology of manufacturing a hydrogen sensor through a simple process in which after a transition metal or an alloy thin film thereof is disposed on the surface of a substrate made of an elastic material, a tensile force is applied to the elastic substrate, so that hydrogen is sensed through a nanogap formed on the thin film.

Currently, studies on a technology of manufacturing a hydrogen sensor having an excellent detection temperature, an excellent initial hydrogen concentration, and excellent reproducibility in addition to a technology of manufacturing a hydrogen sensor using a simple and easy method while an ultra-low price type hydrogen sensor is targeted have been required.

TECHNICAL PROBLEM

A technical objective of the present invention is to provide a gas sensor of which a detection temperature is the room temperature and a method for manufacturing the same.

Another technical objective of the present invention is to provide a gas sensor having high precision sensitivity and a method for manufacturing the same.

Yet another technical objective of the present invention is to provide a gas sensor having a wide measurement concentration range and a method for manufacturing the same.

Yet another technical objective of the present invention is to provide a gas sensor having excellent selectivity and a method for manufacturing the same.

Yet another technical objective of the present invention is to provide a gas sensor having reproducibility and a method for manufacturing the same.

Yet another technical objective of the present invention is to provide a gas sensor having long-term stability and a method for manufacturing the same.

Yet another technical objective of the present invention is to provide a gas sensor having reduced processing costs and a method for manufacturing the same.

The technical objectives of the present invention are not limited to the above description.

TECHNICAL SOLUTION

In order to solve the above-described technical problems, the present invention provides a method of manufacturing a gas sensor.

According to the embodiment, the method of manufacturing a gas sensor may include: preparing a metal nanowire; producing a thermoelectric composite by adding a polymer bead to the metal nanowire and then mechanically mixing the thermoelectric composite and the polymer bead; producing a thermoelectric layer by hot-pressing the thermoelectric composite; forming a first electrode on an upper surface of the thermoelectric layer and forming a second electrode on a lower surface of the thermoelectric layer; and forming a heating catalyst layer on the first electrode.

According to the embodiment, the heating catalyst layer may include Pt/γ-alumina.

According to the embodiment, the heating catalyst layer may include Pd/Edge Oxidized Graphene (EOG) or Pt/EOG.

According to the embodiment, the Pd/EOG or the Pt/EOG may be obtained by preparing an EOG dispersion solution in which an EOG is dispersed, producing a Pd/EOG or Pt/EOG dispersion solution by adding a Pd precursor or a Pt precursor to the EOG dispersion solution and reducing the EOG dispersion solution including the Pd precursor or the Pt precursor, and extracting the Pd/EOG or the Pt/EOG in the form of a paste from the Pd/EOG or Pt/EOG dispersion solution through centrifugation.

According to the embodiment, the EOG dispersion solution may be produced by acid-treating graphite and then dispersing the graphite in an ionic liquid.

According to the embodiment, the preparing of the metal nanowire may include producing a base solution by adding a metal oxide to a solvent and then mechanically mixing the metal oxide and the solvent, producing a source solution including the metal nanowire by adding a reducing agent to the base solution, and then mechanically mixing the reducing agent and the base solution, and extracting the metal nanowire from the source solution through a washing and drying process.

According to the embodiment, in the producing the thermoelectric composite, a thermal treatment process may be performed after the mechanical mixing, so that the metal nanowire may be adsorbed on a surface of the polymer bead due to a surface charge difference.

According to the embodiment, in the method of manufacturing a gas sensor, a Seebeck coefficient of the thermoelectric layer may be adjusted depending on the content of the metal nanowire.

According to the embodiment, in the method of manufacturing a gas sensor, as the content of the metal nanowire increases, the Seebeck coefficient of the thermoelectric layer may increase.

In order to solve the above-described technical problems, the present invention provides a gas sensor.

According to the embodiment, the gas sensor may include a thermoelectric layer, first and second electrodes that are spaced apart from each other with the thermoelectric layer interposed therebetween, and a heating catalyst layer on the first electrode, in which the thermoelectric layer includes a thermoelectric composite in which a metal nanowire is adsorbed on a polymer bead.

According to the embodiment, the heating catalyst layer of the gas sensor may include Pt/γ-alumina.

According to the embodiment, the heating catalyst layer of the gas sensor may include Pd/EOG.

ADVANTAGEOUS EFFECTS

According to the embodiment of the present invention, a method of manufacturing the gas sensor having excellent thermoelectric characteristics may be provided through a step of preparing the metal nanowire, a step of producing the thermoelectric composite by adding the polymer bead to the metal nanowire and then mechanically mixing the polymer bead and the metal nanowire, a step of producing the thermoelectric layer by hot-pressing the thermoelectric composite, a step of forming the first electrode on the upper surface of the thermoelectric layer and forming the second electrode on the lower surface of the thermoelectric layer, and a step of disposing the heating catalyst layer on the first electrode.

First, the thermoelectric layer may be formed by hot-pressing the thermoelectric composite in which the metal wire is uniformly adsorbed on the polymer bead.

Accordingly, since a high contact interface is formed between the polymer beads in the thermoelectric layer, the usage amount of the metal wire may be minimized, so that process costs may be reduced, and the thermoelectric layer having excellent electric conductivity and excellent thermal insulation may be provided.

Further, since process costs of the hot-pressing process for the gas sensor are low as compared to a high-temperature vacuum process according to the related art, the gas sensor according to the embodiment of the present invention may secure price competitiveness for supply of the sensor in the future.

In addition, the Seebeck coefficient of the thermoelectric layer may be adjusted by adjusting the type and the content of the metal nanowire contained in the thermoelectric composite.

Accordingly, sensing characteristics of the gas sensor according to the embodiment of the present invention, such as a detection temperature and a detection concentration, can be easily adjusted by a simple method of adjusting the type and the content of the metal nanowire included in the thermoelectric composite.

Further, when the heating catalyst layer includes the Pd/EOG that is the heating catalyst material, excellent adhesion is achieved due to the high coating strength of the Pd/EOG. Thus, the usage amount of the polymer binder used for manufacturing the gas sensor can be minimized.

Accordingly, the method of manufacturing the gas sensor in which process costs and a process time are reduced may be provided.

In addition, the heating catalyst layer may have excellent thermal conductivity characteristics due to stability of a conjugation structure of the basal plane of the EOG.

Accordingly, when the gas sensor is manufactured using the heating catalyst layer containing the Pd/EOG, heat of reaction with the target gas is easily transferred to the thermoelectric layer, so that the gas sensor having a high electromotive force and a rapid stabilization speed may be provided.

Further, use of the thermal conductivity paste in the gas sensor is minimized due to excellent thermal conductivity characteristics of the gas sensor, so that process costs of the gas sensor may be reduced.

In addition, the gas sensor which easily and precisely measures a low-concentration gas due to excellent thermal conductivity characteristics of the gas sensor may be provided.

DETAILED DESCRIPTION

Figure 1:
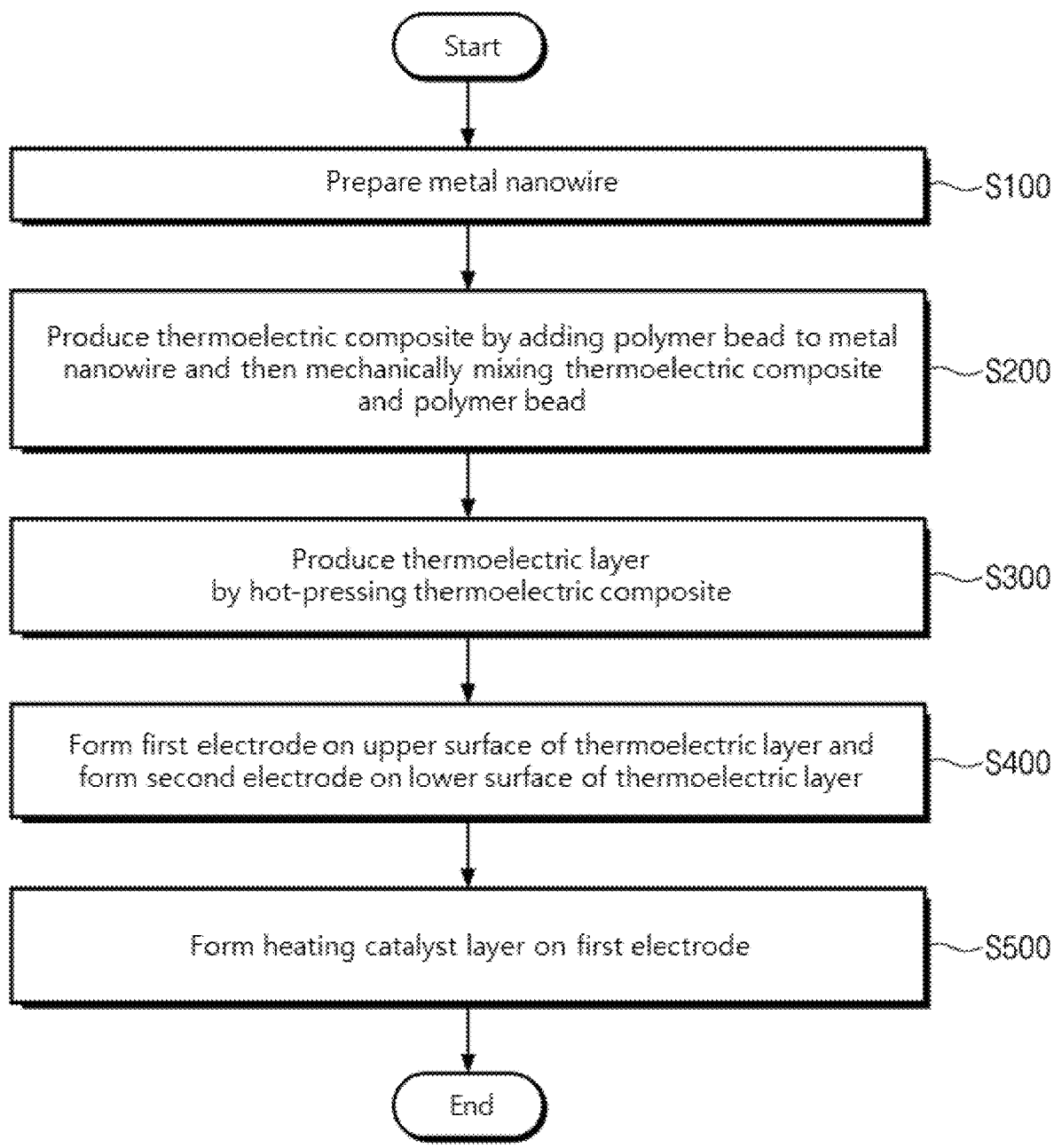
FIG. 1 is a flowchart illustrating a method for manufacturing a gas sensor according to an embodiment of the present invention.

Hereinafter, exemplary embodiments of the present invention will be described in detail with reference to the accompanying drawings.

However, the technical spirit of the present invention is not limited to embodiments described herein but may be embodied in other forms.

Instead, the embodiments described herein are provided such that contents disclosed can be thorough and complete and the spirit of the present invention can be fully transferred to those skilled in the art.

In the present specification, in a case where it is mentioned that a first component is located on a second component, this case means that the first component is directly formed on the second component or the first component is formed on the second component with a third component interposed therebetween.

Further, in the drawings, the thicknesses of films and regions are exaggeratedly illustrated for effective description of the technical contents.

Further, although terms "first", "second", "third", and the like in various embodiments of the present specification are used to describe various components, these components should not be limited by these terms.

These terms have only been used to distinguish one component from another component.

Thus, a component, which is mentioned as a first component in any one embodiment, may be mentioned as a second component in another embodiment.

The embodiments described and exemplified herein include a complementary embodiment therefor.

Further, in the present specification, the term "and/or" is used to mean that a component includes at least one of components listed before and after the term.

in the specification, a singular expression includes a plural expression unless the context is clearly stated otherwise.

Further, the term "include" or "have" is intended to specify presence of features, numbers, steps, components, and combinations thereof stated in the specification, but should not be understood to exclude presence or addition of one or more other features, numbers, steps, components, and combinations thereof.

Further, in the present specification, a metal nanowire is interpreted to include a nanowire made of metal, a nanowire including metal, a nanowire including metal and having semiconductor characteristics, a nanowire including metal and having metal characteristics, and the like.

Further, in the present specification, a "metal oxide" is interpreted as a component containing metal and oxygen.

Further, in the following description of the present invention, when it is determined that detailed description of related widely-known functions or configurations makes the subject matter of the present invention unclear, the detailed description will be omitted.

Figure 2:
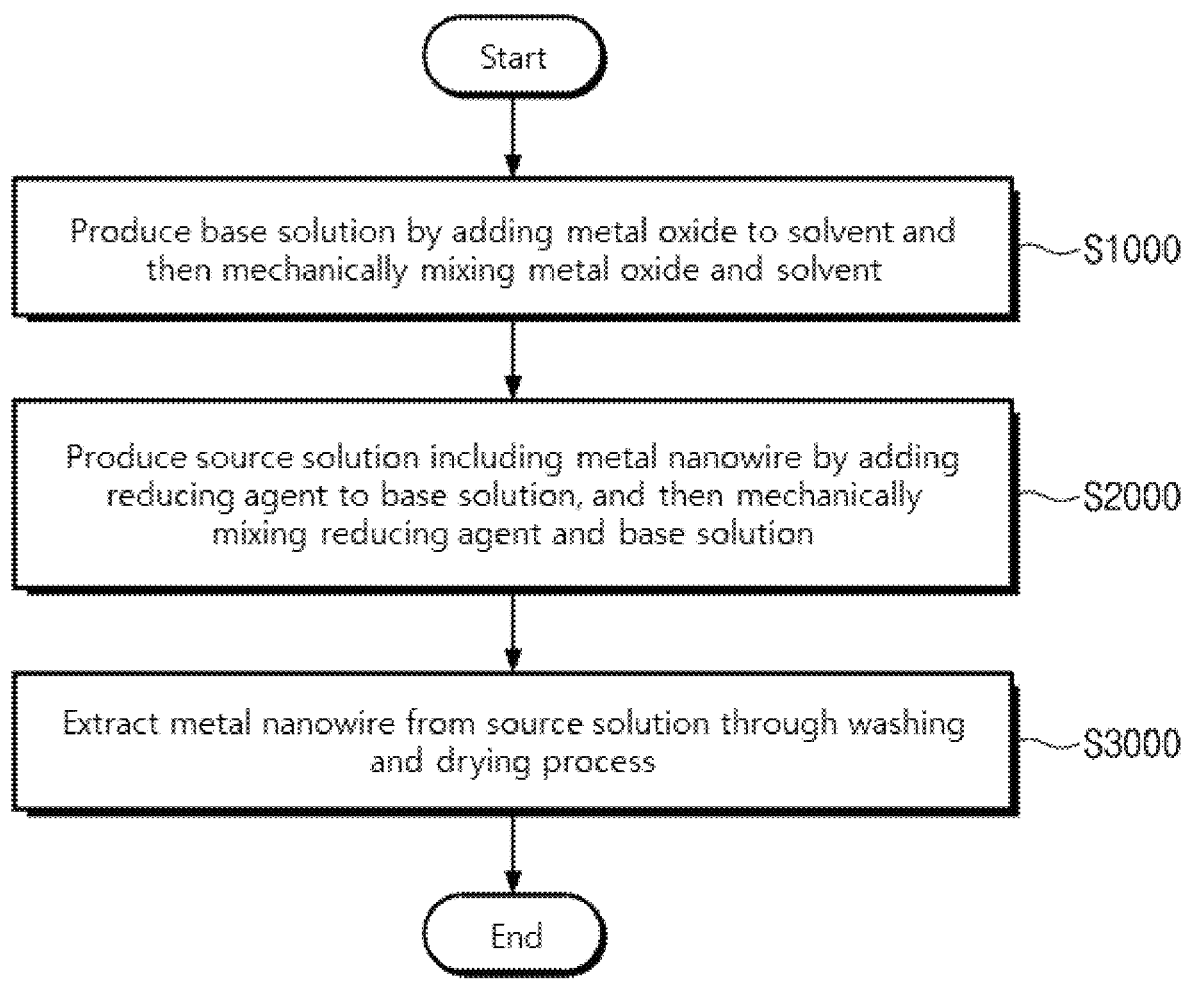
FIG. 2 is a flowchart illustrating a method for manufacturing a metal nanowire according to the embodiment of the present invention.
Figure 3:
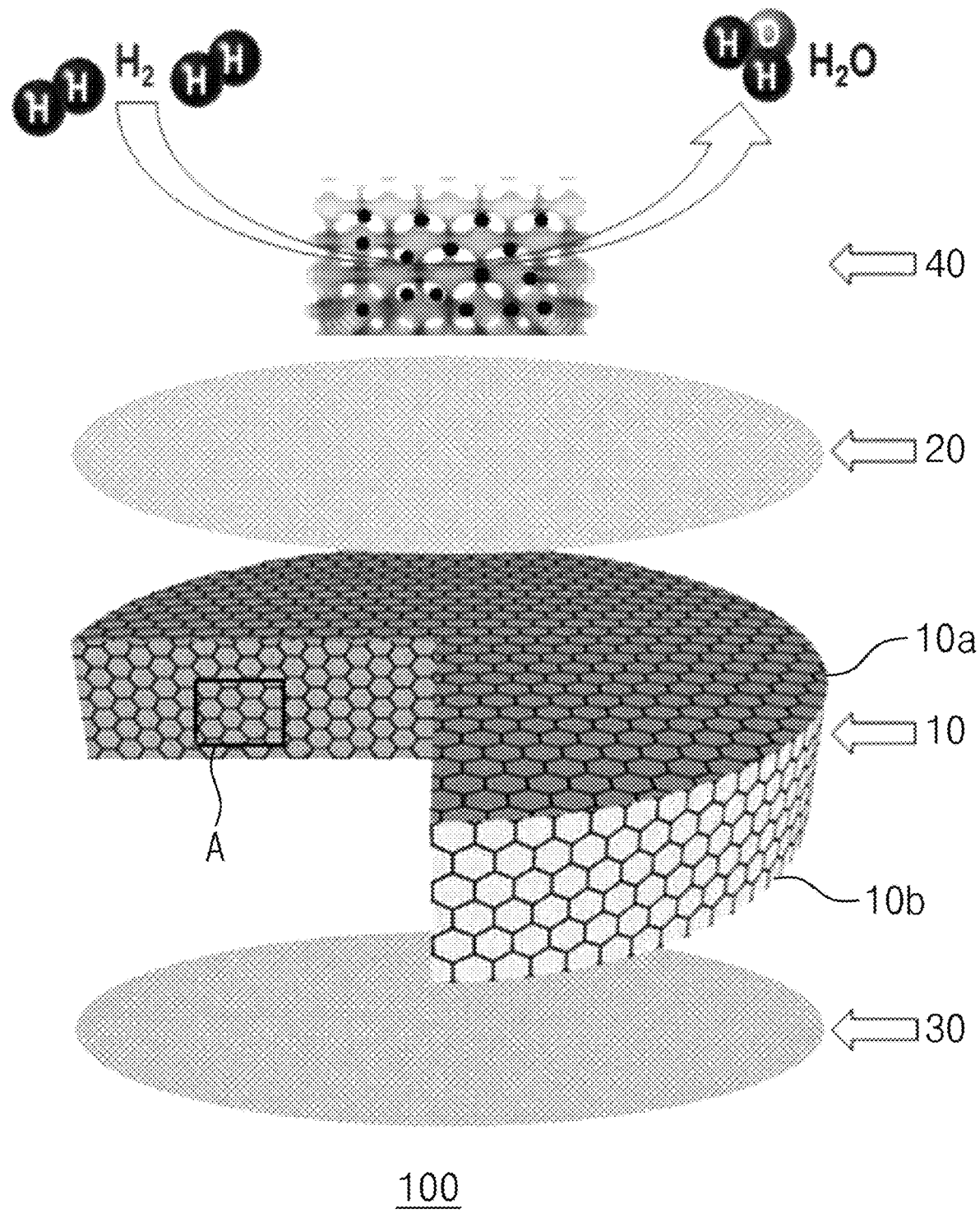
FIG. 3 is a view illustrating the method for manufacturing a gas sensor according to the present invention.
Figure 4:
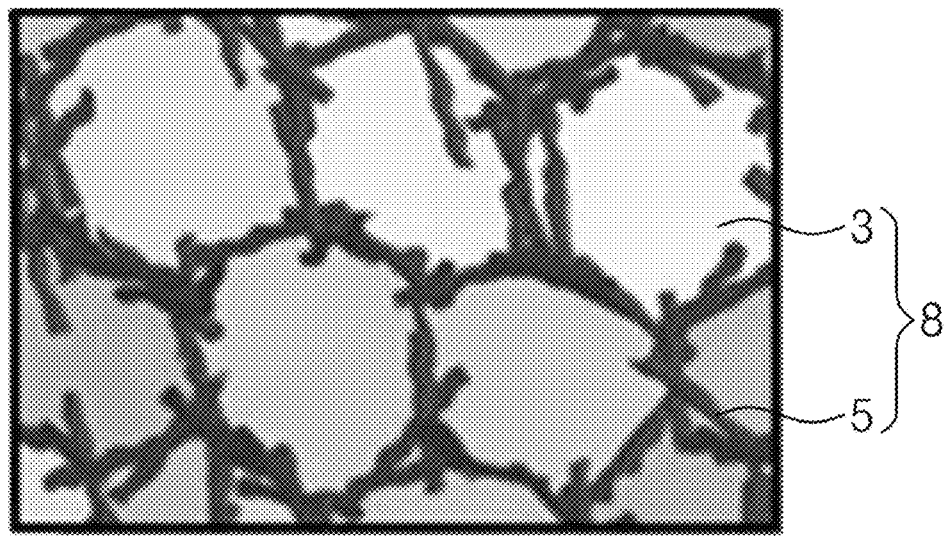
FIG. 4 is an enlarged view illustrating part A of FIG. 3.

FIG. 1 is a flowchart illustrating a method for manufacturing a gas sensor according to an embodiment of the present invention, FIG. 2 is a flowchart illustrating a method for manufacturing a metal nanowire according to the embodiment of the present invention, FIG. 3 is a view illustrating the method for manufacturing a gas sensor according to the present invention, and FIG. 4 is an enlarged view illustrating part A of FIG. 3.

Referring to FIGS. 1 to 4, a metal nanowire 3 may be prepared (S100).

The metal nanowire 3 may be manufactured through a solvothermal method.

Hereinafter, a method of manufacturing the metal nanowire 3 will be described with reference to FIG. 2.

As illustrated in FIG. 2, a base solution may be produced by adding a metal oxide to a solvent and then mechanically mixing the metal oxide and the solvent (S1000).

According to the embodiment, the mechanical mixing may include a stirring process.

According to the embodiment, the metal oxide may include chalcogen or chalcogenide.

For example, the chalcogen may be a compound containing tellurium (Te) or selenium (Se), and the chalcogenide may be a compound containing one or more chalcogens selected from the group consisting of selenium (Se) or tellurium (Te).

Further, the chalcogenide is a binary or higher-order compound containing one or more chalcogens selected from the group consisting of selenium and tellurium, and may include one or more materials selected from the group consisting of BixTey SbxTey, BixSey, SbxSey,(Bi1-mSbm)xSey, PbSe, PbTe, CdSe, ZnSe, PbTeSe, (Bi1-mSbm)xTey, CdTe, ZnTe, La3Te4, AgSbTe2, Ag2Te, AgPb18BiTe20, (GeTe)x(AgSbTe2)1-x (x is a real number smaller than 1), AgxPb18SbTe20 (x is a real number smaller than 1), AgxPb22.5SbTe20 (x is a real number smaller than 1), SbxTe20 (x is a real number smaller than 1), and BixSb2-xTe3 (x is a real number smaller than 2).

Further, the metal oxide may include at least one of $H_2TeO_4$ $2H_2O$ and $Na_2TeO_3$.

According to the embodiment, the solvent may include one or more materials selected from ethylene glycol, diethylene glycol, sodium dodecyl benzene sulfonate, and sodium borohydride.

According to the embodiment, the base solution may be produced by adding 10 g of 99.99% of tellurium dioxide (TeO2) to 99.8% of ethylene glycol anhydride and then stirring the mixture for two hours.

A source solution including the metal nanowire 3 may be produced by adding a reducing agent to the base solution, and then mechanically mixing the reducing agent and the base solution.

In detail, the metal oxide may be reduced by the reducing agent, and at the same time, may be synthesized into a nanowire structure including the metal.

According to the embodiment, the reducing agent may include one or more materials selected from hydroxylamine, pyrrole, polyvinylpyrrolidone, polyethylene glycol, hydrazine hydrate, hydrazine monohydrate, and ascorbic acid.

According to the embodiment, the metal oxide may be synthesized in the form of a nanorod, a nanotube, or a fragment including the metal in addition to the nanowire structure including the metal.

According to the embodiment, the source solution including an one-dimensional shaped tellurium nanowire (Te nanowire) may be produced by adding 50 wt % of hydroxylamine solution in $H_2O$ to the base solution and then stirring the mixture for two hours.

The metal nanowire 3 may be extracted from the source solution through a washing and drying process (S3000).

According to the embodiment, the metal nanowire 3 included in the source solution may be washed through acetone and deionized water.

Further, the washed metal nanowire 3 may be dried in a vacuum oven at a temperature of 80□ for six hours.

Next, referring to FIGS. 1, 3, and 4, a thermoelectric composite 8 may be manufactured by adding a polymer bead 5 to the metal nanowire 3 and then mechanically mixing the metal nanowire 3 and the polymer bead 5.

In detail, a step of manufacturing the thermoelectric composite 8 may include a step of producing a solution including the metal nanowire 3, a step of mechanically mixing the metal nanowire 3 and the polymer bead 5, and a step of performing thermal treatment.

The step of producing the solution including metal nanowire 3 may include dispersing the metal nanowire 3 in the solvent.

According to the embodiment, by an ultrasonicator, the metal nanowire 3 is dispersed in isopropyl alcohol that is the solution for 30 minutes, so that a solution in which the metal nanowire 3 is dispersed may be produced.

The step of mechanically mixing the metal nanowire 3 and the polymer bead 5 may include adding the polymer bead 5 to the solution in which the metal nanowire 3 is dispersed and then mechanically mixing the polymer bead 5 and the solution.

According to the embodiment, the metal nanowire 3 and the polymer bead 5 may be mechanically mixed with each other in a volume ratio of 1:3 to 1:30.

According to the embodiment, the polymer bead 5 may include one or more materials selected from polymethylmethacrylate, polyamide, polypropylene, polyester, polyvinyl chloride, polycarbonate, polyphthalamide, polybutadiene terephthalate, polyethylene terephthalate, polyetylene, polyether ether ketone, and polystyrene.

According to the embodiment, the polymer bead 5 may have an average size of 100 nm to 100 μm.

According to the embodiment, after poly(methyl methacrylate (PMMA) in the form of beads is added to the solution in which the tellurium nanowire that is the metal nanowire 3 is dispersed, the PMMA and the solution may be stirred at a speed of 400 rpm for three hours.

As illustrated in FIG. 4, the step of performing thermal treatment may include manufacturing the thermoelectric composite 8 in which the metal nanowire 3 is adsorbed on the polymer bead 5.

In detail, through the step of performing thermal treatment, the thermoelectric composite 8 may be manufactured by substantially uniformly adsorbing the metal nanowire 3 on the polymer bead 5 due to a surface charge difference while the solvent is removed from the solution in which the metal nanowire 3 and the polymer bead 5 are dispersed.

According to the embodiment, the thermal conductivity of the thermoelectric composite 8 may be 0.1 W/mK to 0.5 W/mk.

According to the embodiment, the thermoelectric composite 8 in which the tellurium nanowire is adsorbed on the PMMA bead may be manufactured by performing thermal treatment of the solution, in which the metal nanowire 3 and the polymer bead 5 are dispersed, in the vacuum oven at a temperature of 80□ for three hours.

According to the embodiment, the Seebeck coefficient of a thermoelectric layer 10 which will be described below may be adjusted according to the content of the metal wire 3.

According to the embodiment, as the content of the metal nanowire 3 increases, the Seebeck coefficient of the thermoelectric layer 10 may increase.

Accordingly, a gas sensor 100 having an excellent thermoelectric effect according to the embodiment of the present invention may be manufactured by adjusting the content of the metal nanowire 3.

The thermoelectric layer 10 may be manufactured by hot-pressing the thermoelectric composite 8 (S300).

In detail, the thermoelectric composite 8 may be hot-pressed by heat and pressure in a temperature range that is equal to or more than the glass transition temperature Tg of the polymer bead 5 and is less than the melting point Tm of the polymer bead 5.

According to the embodiment, the pressure that is applied to the thermoelectric composite 8 together with the heat may be 10 MPa to 1000 MPa.

As described above, since the thermoelectric layer 10 is manufactured by hot-pressing the thermoelectric composite 8, a contact interface between the polymer beads 5 in the thermoelectric layer 10 may increase.

Accordingly, the thermoelectric layer 10 having excellent electrical conductivity and excellent thermal insulation may be manufactured.

According to the embodiment, the thermoelectric layer 10 may be manufactured by hot-pressing the thermoelectric composite 8, in which the tellurium nanowire is adsorbed on the PMMA bead, for 30 minutes at a pressure of 400 MPa at a temperature of 150□.

A first electrode 20 may be formed on an upper surface 10a of the thermoelectric layer 10, and a second electrode 30 may be formed on a lower surface 10b of the thermoelectric layer 10 (S400).

In detail, a step of forming the first electrode 20 and the second electrode 30 may include a step of coating an electrode material on the thermoelectric layer 10 and a step of thermal-treating the electrode material.

The step of coating the electrode material on the thermoelectric layer 10 may include arranging a leading wire connecting the electrode material on the upper surface 10a and the lower surface 10b to each other after the electrode material is coated on the upper surface 10a and the lower surface 10b of the thermoelectric layer 10.

There is no limitation on the type of the electrode material and the type of the leading wire.

For example, the electrode material may be silver paste, and the leading wire may be a copper (Cu) leading wire.

According to the embodiment, the silver paste may be coated on the upper surface 10a and the lower surface 10b of the thermoelectric layer 10.

Further, the silver paste coated on the upper surface 10a and the lower surface 10b may be connected to each other through the copper leading wire.

The step of thermal-treating the electrode material may include forming the first electrode 20 and the second electrode 30 on the upper surface 10a and the lower surface 10b of the thermoelectric layer 10, respectively, by drying the thermoelectric layer 10 coated with the electrode material.

According to the embodiment, the silver paste coated on the upper surface 10a and the lower surface 10b may be thermal-treated and dried by the vacuum oven.

A heating catalyst layer 40 may be formed on the first electrode 20 of the thermoelectric layer 10.

In detail, as a heating catalyst material is coated on the first electrode 20 of the thermoelectric layer 10 and is then dried, the heating catalyst layer 40 may be formed on the thermoelectric layer 10.

According to the embodiment, the heating catalyst layer 40 may include Pt/γ-alumina, Pd/EOG, or Pt/EOG which is the heating catalyst material.

According to the embodiment, the Pd/EOG, which is the heating catalyst material, may be produced through a step of preparing an EOG dispersion solution, a step of producing a Pd/EOG dispersion solution by reducing the EOG dispersion solution, and a step of extracting the Pd/EOG from the Pd/EOG dispersion solution.

The step of preparing the EOG dispersion solution may include dispersing acid-treated graphite in an ionic liquid.

The acid-treated graphite may be graphite of which an edge portion is selectively oxidized.

According to the embodiment, the graphite may be treated with sulfuric acid ($H_2SO_4$), and thus the edge portion of the graphite may be selectively oxidized.

Further, the acid-treated graphite is dispersed in the ionic liquid by a high-pressure homogenizer, so that the EOG dispersion solution may be produced.

The step of producing the Pd/EOG dispersion solution by reducing the EOG dispersion solution may include producing the Pd/EOG dispersion solution by adding a Pd precursor and a reducing agent to the EOG dispersion solution.

According to the embodiment, a solution of $H_2PdCl_4$ that is the Pd precursor may be added to the EOG dispersion solution to reflux the solutions, and at the same time, NaBH4 that is the reducing agent may be added to the EOG dispersion solution in a dropwise method.

Thereafter, the reduction reaction is performed at a temperature of 70□ for one hour, so that the Pd/EOG dispersion solution may be produced.

The step of extracting the Pd/EOG from the Pd/EOG dispersion solution may include obtaining the Pd/EOG in the form of a paste from the Pd/EOG dispersion solution through centrifugation.

According to the embodiment, the Pd/EOG contained in the Pd/EOG dispersion solution is washed and is then extracted in the form of a paste, by a centrifuge.

As described above, when the heating catalyst layer 40 containing the Pd/EOG is formed on the first electrode 20, stickiness is excellent due to a high coating strength of the Pd/EOG, so that usage of a polymer binder can be minimized.

The Pt/EOG may be produced using a Pt precursor in the same manner as the method of producing the Pd/EOG.

Further, excellent thermal conductivity characteristics may be achieved due to a stable conjugation structure of a basal plane of the EOG.

Accordingly, when a thermochemical hydrogen sensor (TCH) is produced using the heating catalyst layer 40 containing the Pd/EOG, heat of reaction with hydrogen $H_2$ is easily transferred to the thermoelectric layer 10, so that a high electromotive force and a rapid stabilization speed can be obtained.

Further, the usage amount of thermal conductivity paste in the sensor is minimized due to excellent thermal conductivity characteristics, so that processing costs of the gas sensor 100 can be reduced.

Further, a method of manufacturing the gas sensor 100 which can precisely measure hydrogen gas at a low concentration may be provided.

Hereinafter, a gas sensor according to the embodiment of the present invention will be described.

In description of the gas sensor according to the embodiment of the present invention, a portion overlapping with the description of the method of manufacturing the gas sensor according to the embodiment of the present invention, illustrated in FIGS. 1 to 4, will be described with reference to FIGS. 1 to 4.

Referring to FIG. 3, the gas sensor 100 according to the embodiment of the present invention may include the thermoelectric layer 10, the first electrode 20, the second electrode 30, and the heating catalyst layer 40.

As described with reference to FIGS. 1 to 4, the thermoelectric layer 10 may include the thermoelectric composite 8 in which the metal nanowire 3 is adsorbed on the polymer bead 5.

As described above, since the thermoelectric layer 10 is produced by the hot pressing, a wide contact interface can be formed between the polymer beads 5.

Accordingly, the thermoelectric layer 10 having excellent electrical conductivity and excellent thermal insulation may be provided.

According to the embodiment, the metal oxide may include chalcogen or chalcogenide.

For example, the chalcogen may be a compound containing tellurium (Te) or selenium (Se), and the chalcogenide may be a compound containing one or more chalcogens selected from the group consisting of selenium (Se) or tellurium (Te).

Further, the chalcogenide is a binary or higher-order compound containing one or more chalcogens selected from the group consisting of selenium and tellurium, and may include one or more materials selected from the group consisting of BixTey SbxTey, BixSey, SbxSey,(Bi1-mSbm)xSey, PbSe, PbTe, CdSe, ZnSe, PbTeSe, (Bi1-mSbm)xTey, CdTe, ZnTe, La3Te4, AgSbTe2, Ag2Te, AgPb18BiTe20, (GeTe)x(AgSbTe2)1-x (x is a real number smaller than 1), AgxPb18SbTe20 (x is a real number smaller than 1), AgxPb22.5SbTe20 (x is a real number smaller than 1), SbxTe20 (x is a real number smaller than 1), and BixSb2-xTe3 (x is a real number smaller than 2).

Further, according to the embodiment, the polymer bead 5 may include one or more materials selected from polymethylmethacrylate, polyamide, polypropylene, polyester, polyvinyl chloride, polycarbonate, polyphthalamide, polybutadiene terephthalate, polyethylene terephthalate, polyetylene, polyether ether ketone, and polystyrene.

According to the embodiment, an average size of the polymer bead 5 may be 100 nm to 100 μm.

The first electrode 20 and the second electrode 30 may be spaced apart from each other with the thermoelectric layer 10 interposed therebetween.

In detail, the first electrode 20 may be disposed on the upper surface 10a of the thermoelectric layer 10, and the second electrode 30 may be disposed on the lower surface 10b of the thermoelectric layer 10.

The type of the electrode material contained in the first electrode 20 and the second electrode 30 is not limited.

As described above, the first electrode 20 and the second electrode 30 may include silver paste.

The heating catalyst layer 40 may be disposed on the first electrode 20.

According to the embodiment, the heating catalyst layer 40 may include Pt/γ-alumina or Pd/EOG which is the heating catalyst material.

As described above, when the heating catalyst layer 40 includes the Pd/EOG, excellent adhesion is achieved due to the high coating strength of the Pd/EOG. Thus, when the gas sensor 100 is manufactured, the usage amount of the polymer binder can be minimized.

Further, excellent thermal conductivity characteristics may be achieved due to a stable conjugation structure of the basal plane of the EOG.

Accordingly, when the thermochemical hydrogen sensor (TCH) is manufactured using the heating catalyst layer 40 containing the Pd/EOG, the heat of reaction with hydrogen $H_2$ can be easily transferred to the thermoelectric layer 10, so that a high electromotive force and a rapid stabilization speed can be obtained.

In addition, due to excellent thermal conductivity characteristics of the gas sensor 100, the usage amount of the thermal conductivity paste in the gas sensor 100 can be minimized, and hydrogen gas at a low concentration can be precisely measured.

As described with reference to FIGS. 1 to 4, the gas sensor 100 may further include the leading wire.

The first electrode 20 and the second electrode 30, which are spaced apart from each other with the thermoelectric layer 10 interposed therebetween, may be connected to each other by the leading wire.

A gas sensing mechanism of the gas sensor 100 according to the embodiment of the present invention may include a step of generating a temperature difference in the thermoelectric layer 10 by target gas and a step of generating an electromotive force between the first electrode 20 and the second electrode 30 due to the temperature difference.

The step of generating the temperature difference in the thermoelectric layer 10 may include generating the temperature difference in the thermoelectric layer 10 due to heat of reaction by reaction of the target gas and the heating catalyst material of the heating catalyst layer 40, when the target gas is provided to the gas sensor 100.

The step of generating the electromotive force between the first electrode 20 and the second electrode 30 may include generating the electromotive force between the first electrode 20 and the second electrode 30 due to the temperature difference generated in the thermoelectric layer 10, and sensing the concentration of the target gas due to the electromotive force.

As described above, in the case of the gas sensor 100 manufactured using the thermoelectric layer 10 containing the Pd/EOG, the heat of reaction generated in the thermoelectric layer 10 is easily transferred to the thermoelectric layer 10, so that the gas sensor 100 can perform precise measurement at a rapid response speed even when being exposed to the target gas at a low concentration.

Unlike the above-described embodiment of the present invention, in the related art, thin film-based researches are actively being conducted for manufacturing a thermoelectric hydrogen sensor.

In particular, researches on manufacturing of a device using platinum (Pt) or palladium (Pd) as a catalyst layer of a SiGe thin film and the thermoelectric hydrogen sensor have been spotlighted.

However, there is a problem in that the above-described manufacturing of the thermoelectric hydrogen sensor is performed in methods, in which a high-vacuum process is required, such as sputtering, beam evaporation, and thermal evaporation.

In the case of the hydrogen sensor based on the SiGe thin film, there is difficulty in that since the Seebeck coefficient at a high temperature is high due to characteristics of the material itself, when being actually operated, the sensor should be operated under a high temperature condition using a Pt heater.

Further, since a palladium (Pd)-based hydrogen sensor not only requires a high temperature condition and a high vacuum condition in a material and sensor manufacturing process but also requires use of expensive palladium (Pd) nanoparticles and nanowires, it is difficult to manufacture a low-cost sensor.

In addition, the palladium (Pd)-based hydrogen sensor has a problem in that when the hydrogen sensor is repeatedly exposed to hydrogen gas, performance deteriorates due to a rapid phase change.

As described above, according to the embodiment of the present invention, a method of manufacturing the gas sensor 100 having excellent thermoelectric characteristics may be provided through a step of preparing the metal nanowire 3, a step of producing the thermoelectric composite 8 by adding the polymer bead 5 to the metal nanowire 3 and then mechanically mixing the polymer bead 5 and the metal nanowire 3, a step of producing the thermoelectric layer 10 by hot-pressing the thermoelectric composite 8, a step of forming the first electrode 20 on the upper surface 10a of the thermoelectric layer 10 and forming the second electrode 30 on the lower surface 10b of the thermoelectric layer 10, and a step of disposing the heating catalyst layer 40 on the first electrode 20.

First, the thermoelectric layer 10 may be formed by hot-pressing the thermoelectric composite 8 in which the metal wire 3 is uniformly adsorbed on the polymer bead 5.

Accordingly, since a high contact interface is formed between the polymer beads 5 in the thermoelectric layer 10, the usage amount of the metal wire 3 may be minimized, so that process costs may be reduced, and the thermoelectric layer 10 having excellent electric conductivity and excellent thermal insulation may be provided.

Further, since process costs of the hot-pressing process for the gas sensor 100 are low as compared to a high-temperature vacuum process according to the related art, the gas sensor according to the embodiment of the present invention may secure price competitiveness for supply of the sensor in the future.

In addition, the Seebeck coefficient of the thermoelectric layer 10 may be adjusted by adjusting the type and the content of the metal nanowire 3 contained in the thermoelectric composite 8.

Accordingly, sensing characteristics of the gas sensor 100 according to the embodiment of the present invention, such as a detection temperature and a detection concentration, can be easily adjusted by a simple method of adjusting the type and the content of the metal nanowire 3 included in the thermoelectric composite 8.

Further, when the heating catalyst layer 40 includes the Pd/EOG that is the heating catalyst material, excellent adhesion is achieved due to the high coating strength of the Pd/EOG. Thus, the usage amount of the polymer binder used for manufacturing the gas sensor 100 can be minimized.

Accordingly, the method of manufacturing the gas sensor 100 in which process costs and a process time are reduced may be provided.

In addition, the heating catalyst layer 40 may have excellent thermal conductivity characteristics due to stability of a conjugation structure of the basal plane of the EOG.

Accordingly, when the gas sensor 100 is manufactured using the heating catalyst layer 40 containing the Pd/EOG, heat of reaction with the target gas is easily transferred to the thermoelectric layer 10, so that the gas sensor 100 having a high electromotive force and a rapid stabilization speed may be provided.

Further, use of the thermal conductivity paste in the gas sensor 100 is minimized due to excellent thermal conductivity characteristics of the gas sensor 100, so that process costs of the gas sensor may be reduced.

In addition, the gas sensor 100 which easily and precisely measures a low-concentration gas due to excellent thermal conductivity characteristics of the gas sensor may be provided.

Hereinafter, characteristic evaluation of the gas sensor according to the embodiment of the present invention will be described.

Method of producing thermoelectric composite according to embodiment

The base solution is produced by adding 10 g of 99.99% of tellurium dioxide ($TeO_2$) to 99.8% of ethylene glycol anhydride and then stirring tellurium dioxide and ethylene glycol anhydride for two hours.

A source solution containing an one-dimensional shaped tellurium (Te) nanowire is produced by adding 50 wt % of hydroxylamine solution in H₂O to the base solution using a micro pipet, and then stirring the mixture for two hours.

The tellurium nanowire having the size of about 200 nm is produced by washing the tellurium nanowire contained in the source solution using acetone and deionized water and then drying the washed tellurium nanowire for six hours using a vacuum oven at a temperature of 80☐.

A solution in which the tellurium nanowire is dispersed is produced by dispersing the tellurium nanowire in isopropyl alcohol that is a solvent for 30 minutes using the ultrasonicator.

After the PMMA in the form of a bead is added to the solution in which the tellurium nanowire is dispersed, the mixture is stirred for three hours at a speed of 400 rpm.

Thereafter, the thermoelectric composite, in which the tellurium nanowire is adsorbed on the PMMA bead, according to the embodiment of the present invention is produced by performing thermal treatment for three hours in the vacuum oven at a temperature of 80☐.

Method of producing thermoelectric composite according to comparative example

The thermoelectric composite is produced according to the method of producing a thermoelectric composite according to the embodiment, and the thermoelectric composite according to a comparative example for the embodiment of the present invention is produced using the PMMA in the form of resin instead of the PMMA in the form of a bead.

Method of manufacturing gas sensor according to embodiments

A thermoelectric layer is produced by hot-pressing the thermoelectric composite produced according to the production method according to the embodiment, for 30 minutes at a pressure of 400 MPa at a temperature of 150☐.

After the silver pastes are coated on the upper surface and the lower surface of the thermoelectric layer, the silver pastes coated on the upper surface and the lower surface are connected to each other through the copper (Cu) leading wire.

Thereafter, as the thermal treatment is performed using the vacuum oven, the first and second electrodes are formed on the upper surface and the lower surface of the thermoelectric layer.

In order to form the heating catalyst layer on the first electrode, the Pd/EOG that is the heating catalyst material is produced.

First, the EOG dispersion solution is produced by treating the graphite with sulfuric acid (H2SO4), selectively oxidizing an edge portion of the graphite, and then dispersing the graphite in the ionic liquid through the high pressure homogenizer.

The Pd/EOG dispersion solution is produced by adding NaBH4 that is the reducing agent to the solution in a dropwise method while adding the solution of H2PdCl4 that is the Pd precursor to the EOG dispersion solution to reflux the solutions, and then reducing the solution for one hour at a temperature of 70☐.

The Pd/EOG contained in the Pd/EOG dispersion solution is washed by using the centrifuge, and is then extracted in the form of a paste.

The gas sensor according to a first embodiment of the present invention is manufactured by coating the produced Pd/EOG on the first electrode, and then forming the heating catalyst layer on the first electrode by drying the coated Pd/EOG.

Further, the gas sensor according to a second embodiment of the present invention is manufactured according to the method of manufacturing a gas sensor according to the embodiment, but is manufactured by forming the heating catalyst layer using Pt/γ-alumina instead of the Pd/EOG as the heating catalyst material.

Figure 5:
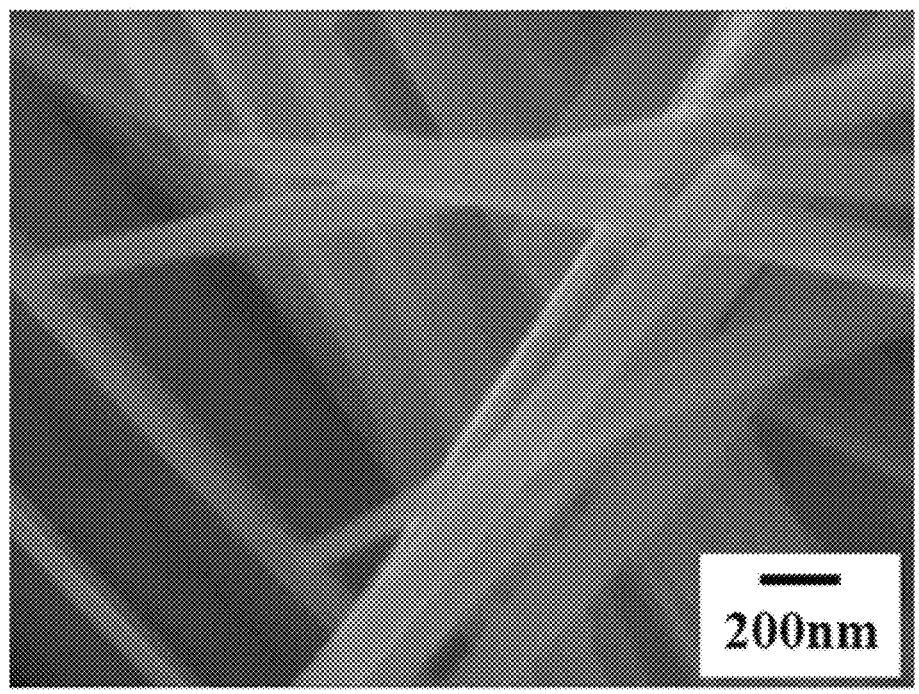
FIG. 5 is an SEM image of a metal wire according to the embodiment of the present invention.

FIG. 5 is an SEM image of a metal wire according to the embodiment of the present invention.

The tellurium nanowire is produced using tellurium dioxide (TeO2) according to the method of producing a thermoelectric composite according to the embodiment.

A detailed image of the surface of the metal wire produced according to the embodiment of the present invention is measured using a scanning electron microscope (SEM) apparatus.

Referring to FIG. 5, it is identified that the tellurium nanowire having the size of about 200 nm is formed.

From this, according to the embodiment of the present invention, it can be identified that when the metal nanowire is produced according to a solvothermal method, the metal nanowire can be easily produced in a simpler method than a process according to the related art, which requires a high-temperature vacuum process.

Figure 6:
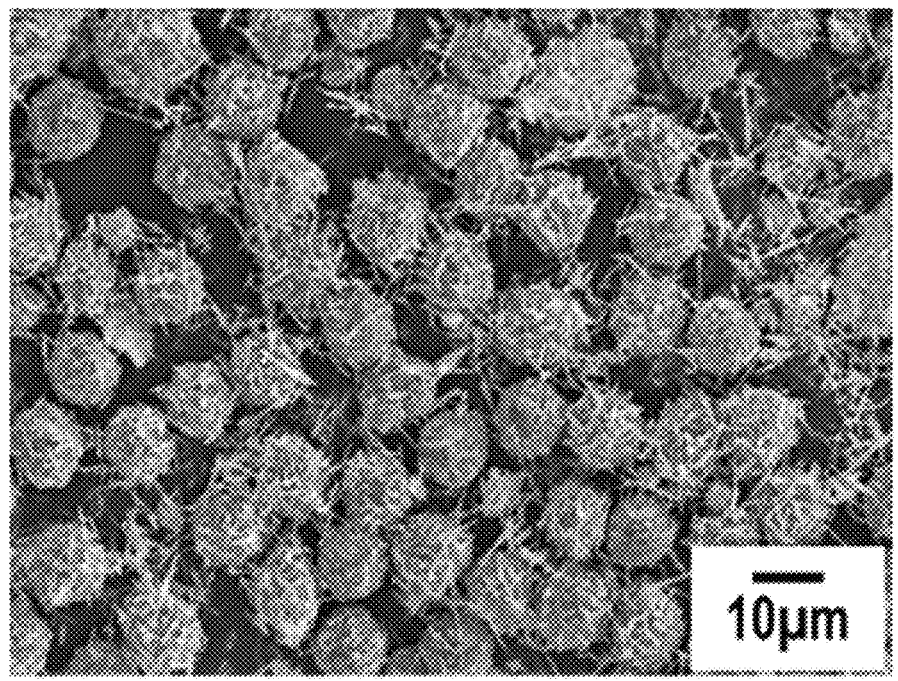
FIG. 6 is an SEM image of a thermoelectric composite according to the embodiment of the present invention.

FIG. 6 is an SEM image of a thermoelectric composite according to the embodiment of the present invention.

According to the method of producing a thermoelectric composite according to the embodiment, the thermoelectric composite in which the tellurium nanowire is adsorbed on the surface of the PMMA bead is produced.

A detailed image of the surface of the thermoelectric composite produced according to the embodiment of the present invention is measured using the scanning electron microscope (SEM) device.

Referring to FIG. 6, it is identified that the tellurium nanowire that is the metal nanowire is uniformly adsorbed on the surface of the PMMA bead that is the polymer bead.

From this, it can be identified that the solution, in which the tellurium nanowire and the PMMA bead are dispersed, is thermally treated, so that the tellurium nanowire is uniformly adsorbed on the PMMA bead due to a surface charge difference while the solvent is removed.

Accordingly, it is identified that despite use of a small amount of the metal nanowire, the thermoelectric composite having excellent thermoelectric characteristics may be produced.

Figure 7A:
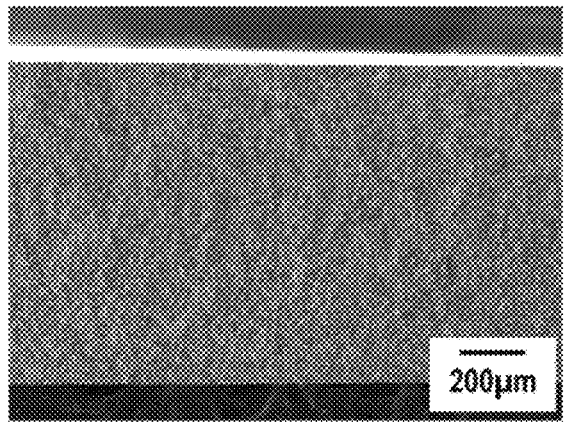
FIGS. 7A and 7B are SEM images of a thermoelectric layer according to the present invention.
Figure 7B:
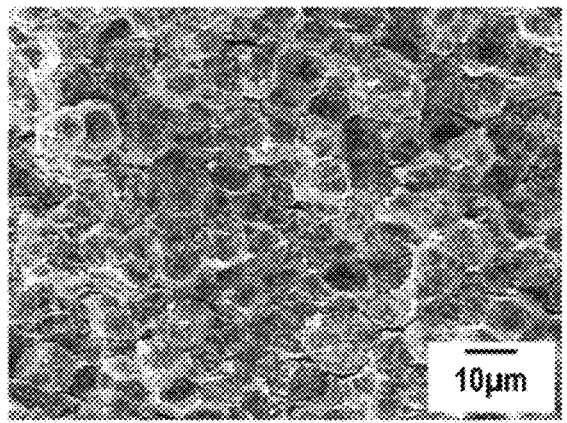

FIGS. 7A and 7B are SEM images of a thermoelectric layer according to the present invention.

In detail, FIG. 7A is an SEM image of the thermoelectric layer under a low magnification condition according to the embodiment of the present invention, and FIG. 7B is an SEM image of the thermoelectric layer under a high magnification condition according to the embodiment of the present invention.

According to the method of manufacturing a gas sensor according to the embodiment, the thermoelectric layer according to the embodiment of the present invention is produced by hot-pressing the thermoelectric composite in which the tellurium nanowire is adsorbed on the PMMA bead.

A detailed image of the surface of the thermoelectric composite produced according to the embodiment of the present invention is measured using the scanning electron microscope (SEM) device.

Referring to FIGS. 7A and 7B, it is identified that a contact interface between the PMMA beads in the thermoelectric layer is increased by hot-pressing the thermoelectric composite.

Accordingly, it can be identified that despite use of a small amount of the tellurium nanowire, the thermoelectric layer having excellent electric conductivity and excellent thermal insulation can be produced.

Figure 8:
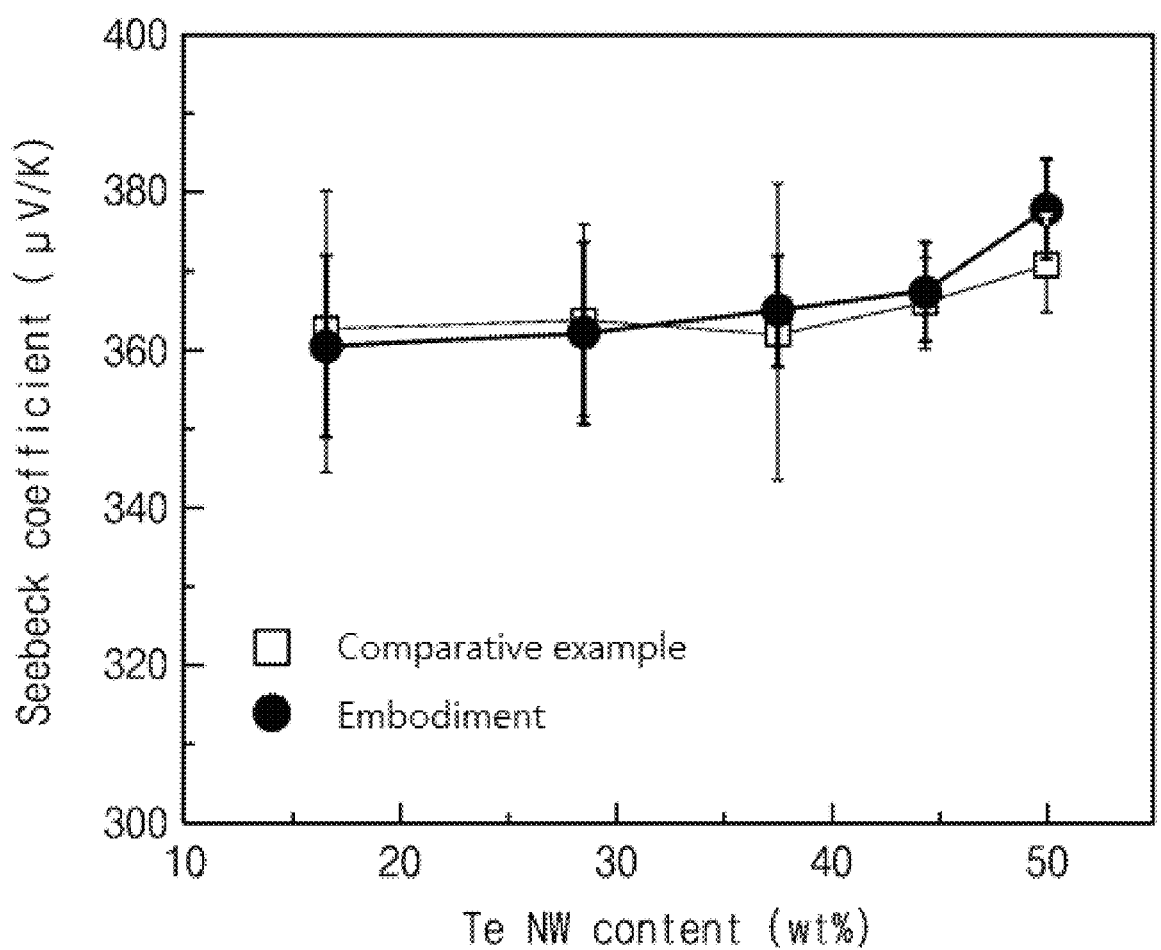
FIG. 8 is a graph depicting values of Seebeck coefficients according to contents of nanowires included in the thermoelectric composite according to the embodiment of the present invention and a comparative example for the embodiment.

FIG. 8 is a graph depicting values of Seebeck coefficients according to contents of nanowires included in the thermoelectric composite according to the embodiment of the present invention and a comparative example for the embodiment.

According to the method of producing the thermoelectric composite according to the embodiment and the comparative example, the thermoelectric composite using the PMMA in the form of a bead according to the embodiment of the present invention and the thermoelectric composite using the PMMA in the form of resin according to the comparative example for the embodiment of the present invention are produced.

Thermoelectric characteristics are compared and analyzed by deducing the Seebeck coefficient value according to the content (wt %) of the metal nanowires included in the thermoelectric composites according to the embodiment and the comparative example for the embodiment.

Referring to FIG. 8, it is identified that the Seebeck coefficient increases as the contents of the metal nanowires included in the thermoelectric composite according to the embodiment of the present invention and the thermoelectric composite according to the comparative example for the embodiment of the present invention increase.

Further, it is identified that the Seebeck coefficient value according to the content of the metal nanowire of the thermoelectric composite, in which the metal nanowire is adsorbed on the polymer bead, according to the embodiment of the present invention is larger than the Seebeck coefficient value according to the content of the metal nanowire of the thermoelectric composite, in which the metal nanowire is added to the polymer in the form of resin, according to the comparative example for the embodiment of the present invention.

From this, according to the embodiment of the present invention, it can be identified that the thermoelectric composite in which the metal nanowire is adsorbed on the polymer in the form of a bead has excellent thermoelectric characteristics.

Figure 9:
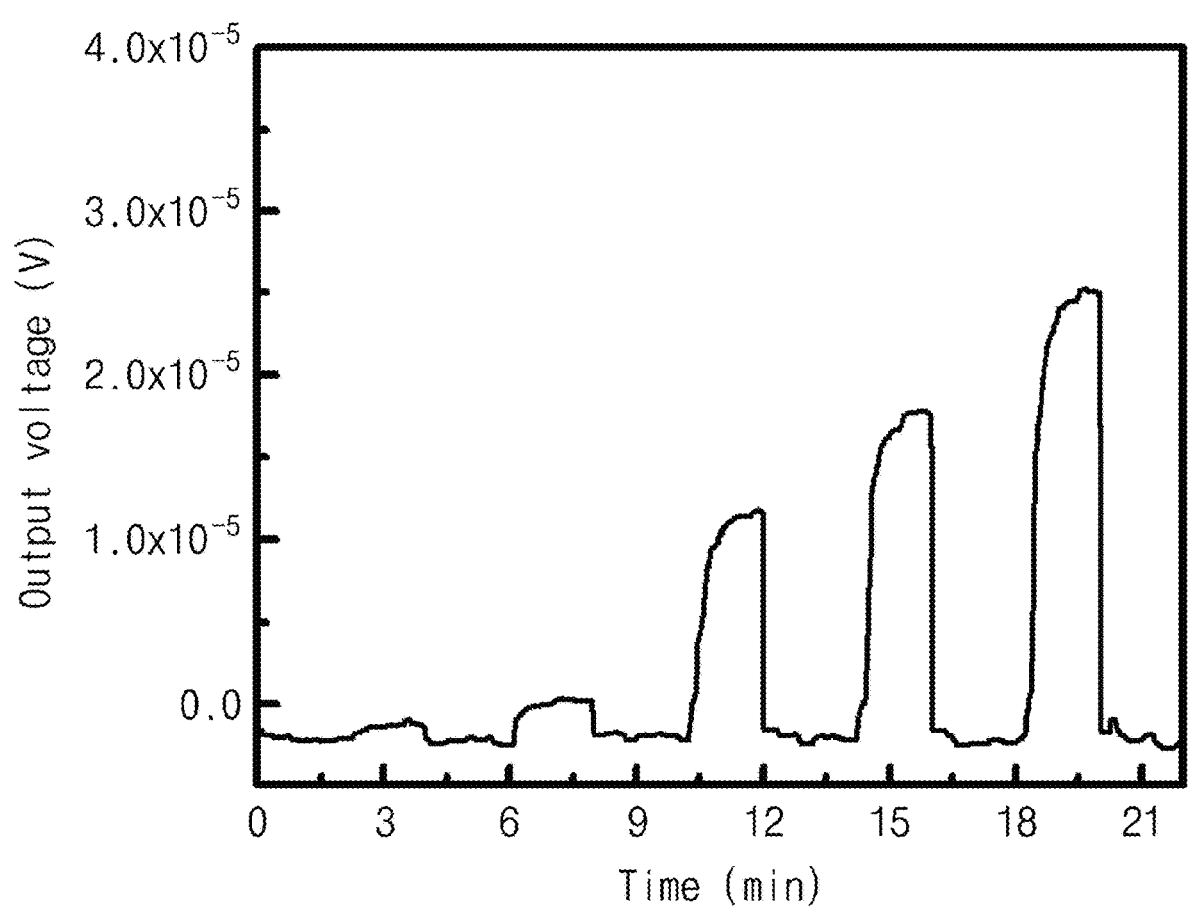
FIG. 9 is a graph depicting a value of an electromotive force (an output voltage) according to a time of a gas sensor according to a first embodiment of the present invention.

FIG. 9 is a graph depicting a value of an electromotive force (an output voltage) according to a time of a gas sensor according to a first embodiment of the present invention;

According to the method of manufacturing a gas sensor according to the embodiment, the gas sensor according to the first embodiment of the present invention is manufactured by forming the heating catalyst layer containing 0.001225 g of the Pt/γ-alumina as the heating catalyst material.

In a condition in which the hydrogen (H2) gas is the target gas, a flow rate is 500 sccm, and a gas on/off time is 120 sec/120 sec, an electromotive force according to a time of the gas sensor, in which the thermoelectric layer contains the Pt/γ-alumina, according to the first embodiment of the present invention is measured.

Referring to FIG. 9, it is identified that the hydrogen gas having a concentration of 1% to 5% is clearly sensed by the gas sensor according to the first embodiment of the present invention.

Figure 10:
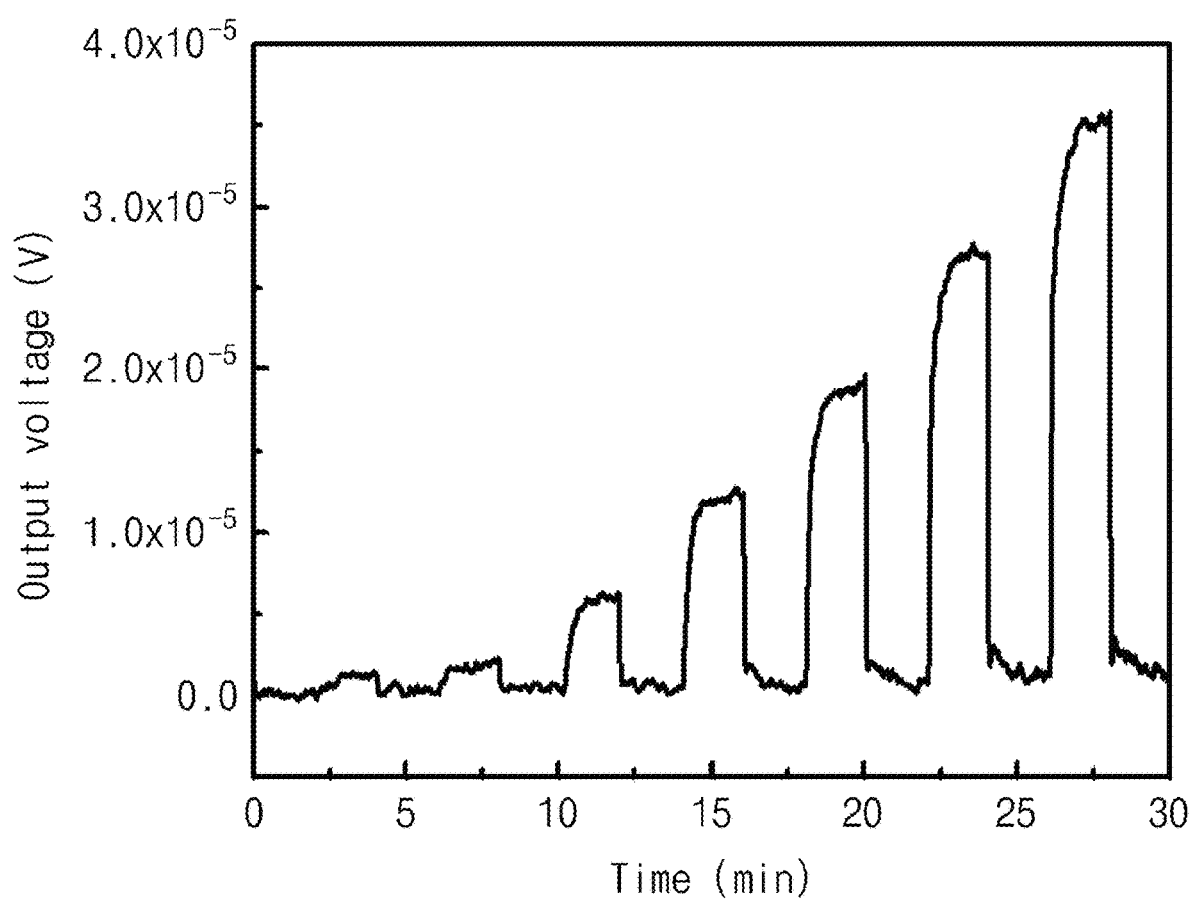
FIG. 10 is a graph depicting a value of an electromotive force according to a time of a gas sensor according to a second embodiment of the present invention.

FIG. 10 is a graph depicting a value of an electromotive force according to a time of a gas sensor according to a second embodiment of the present invention.

According to the method of manufacturing a gas sensor according to the embodiment, the gas sensor according to the second embodiment of the present invention is manufactured by forming the heating catalyst layer containing 0.0005 g of the Pd/EOG as the heating catalyst material.

In a condition in which the hydrogen (H2) gas is the target gas, a flow rate is 500 sccm, and a gas on/off time is 120 sec/120 sec, an electromotive force according to a time of the gas sensor, in which the thermoelectric layer contains the Pd/EOG, according to the second embodiment of the present invention is measured.

Referring to FIG. 10, it is identified that the hydrogen gas having a concentration of 0.8% to 10% is clearly sensed by the gas sensor according to the second embodiment of the present invention.

It is identified from the results of FIGS. 9 and 10 that the gas sensor, in which the heating catalyst layer includes the Pd/EOG, according to the second embodiment has a clearer sensing signal at a low concentration and a wider sensing concentration range, as compared to the gas sensor, in which the heating catalyst layer includes the Pt/γ-alumina, according to the first embodiment.

From this, it is determined that the gas sensor according to the embodiment of the present invention, which can measure a lower and concentration and a concentration within a wider range, can be provided by adjusting the type and the content of the metal wire, the thickness of the thermoelectric layer, and/or heating characteristics of the heating catalyst layer.

Figure 11:
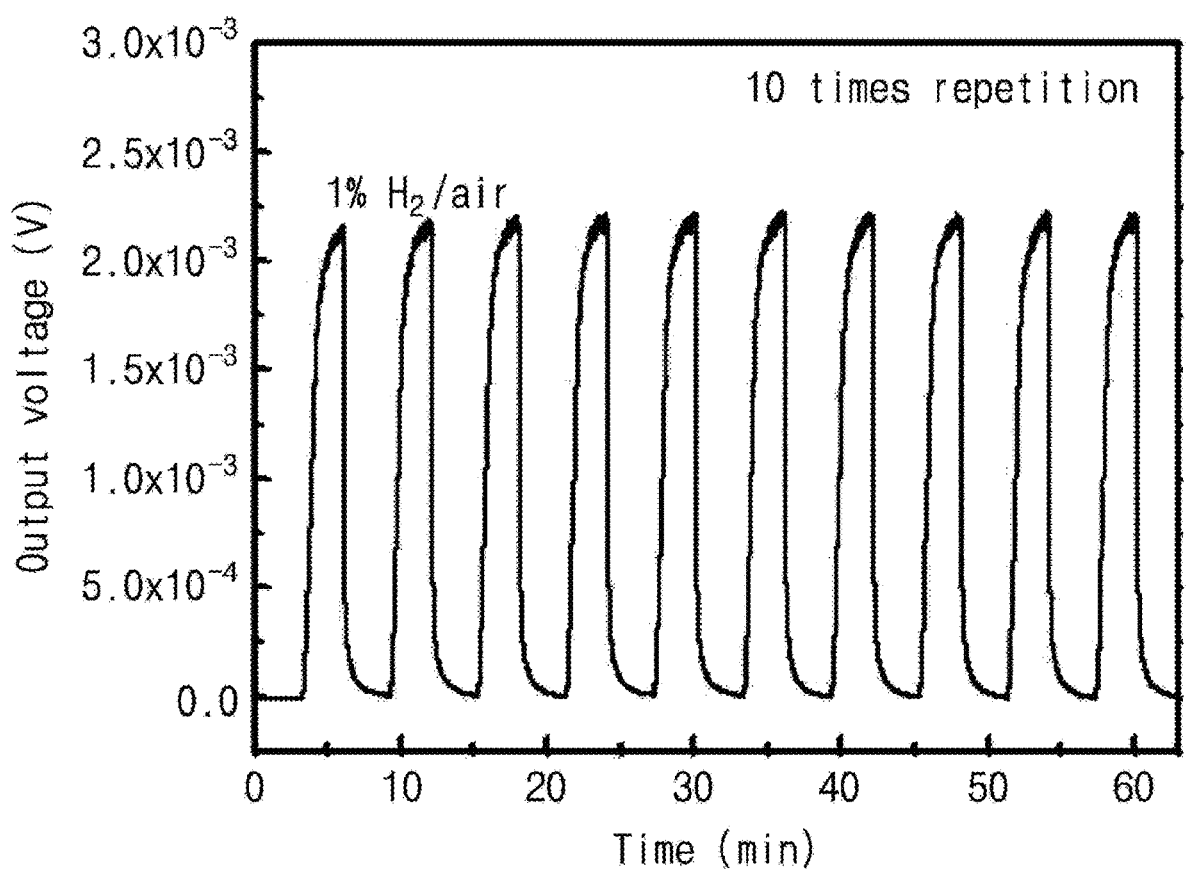
FIG. 11 is a graph depicting a value of an electromotive force according to a time when hydrogen gas and dried air are repeatedly provided to the gas sensor according to the embodiment of the present invention.

FIG. 11 is a graph depicting a value of an electromotive force according to a time when hydrogen gas and dried air are repeatedly provided to the gas sensor according to the embodiment of the present invention.

After 1 vol % of the hydrogen gas and dry air are alternately and repeatedly provided to the gas sensor manufactured according to the method of manufacturing a gas sensor according to the embodiment 10 times, an electromotive force according to a time of the gas sensor is measured.

Repeatability characteristics of the gas sensor according to the embodiment of the present invention are analyzed by measuring a change in the electromotive force according to the time of the gas sensor.

Referring to FIG. 11, it is identified that when the hydrogen gas is repeatedly provided to the gas sensor according to the embodiment of the present invention 10 times, the change in the electromotive force is within about 3%.

In other words, it is identified that the gas sensor according to the embodiment of the present invention has no significant difference in the electromotive force despite the repeated exposure of the hydrogen gas.

From this, it is identified that the gas sensor according to the embodiment of the present invention has excellent repeatability characteristics.

Figure 12:
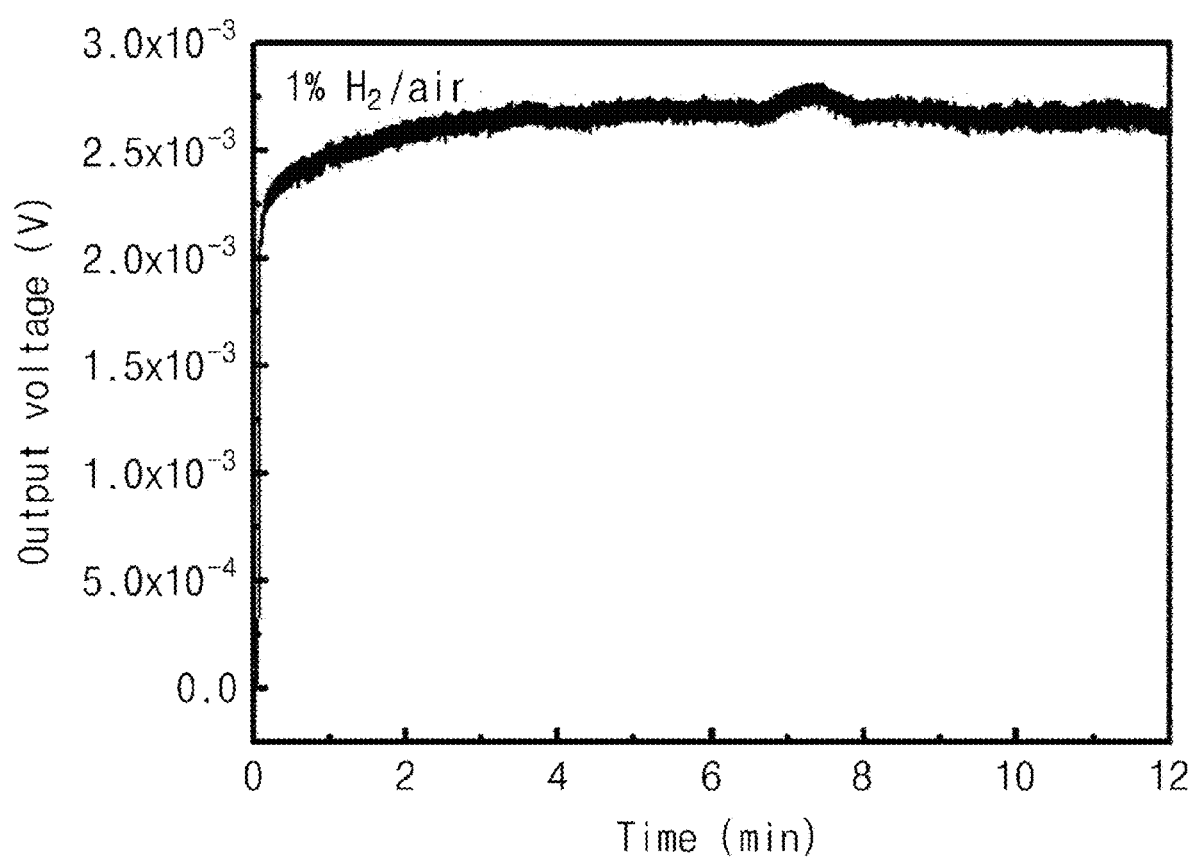
FIG. 12 is a graph depicting a value of an electromotive force according to a time when the hydrogen gas is consistently provided to the gas sensor according to the embodiment of the present invention.

FIG. 12 is a graph depicting a value of an electromotive force according to a time when the hydrogen gas is consistently provided to the gas sensor according to the embodiment of the present invention.

While 3 vol % of the hydrogen gas is continuously provided to the gas sensor manufactured according to the method of manufacturing a gas sensor according to the embodiment for 12 hours, the electromotive force of the gas sensor is measured.

Reliability characteristics of the gas sensor according to the embodiment of the present invention are analyzed by measuring the change in the electromotive force according to the time of the gas sensor.

Referring to FIG. 12, it is identified that when the hydrogen gas is continuously provided to the gas sensor according to the embodiment of the present invention, there is no significant difference in the electromotive force of the gas sensor.

In other words, it is identified that even when the hydrogen gas is continuously provided to the gas sensor according to the embodiment of the present invention, no significant error occurs in the electromotive force of the gas sensor.

From this, it is identified that the gas sensor according to the embodiment of the present invention has excellent reliability characteristics.

In this way, it is identified that when the gas sensor is manufactured using the thermoelectric layer manufactured by hot-pressing the thermoelectric composite in which the metal wire is adsorbed on the polymer bead and the heating catalyst layer including the Pt/γ-alumina or the Pd/EOG according to the embodiment of the present invention, the gas sensor has excellent electric conductivity and excellent thermal insulation despite use of a small amount of the metal wire.

Further, according to the embodiment of the present invention, the method of manufacturing a gas sensor may be provided in which low-concentration hydrogen gas can be precisely measured, and excellent repeatability and excellent reliability are achieved.

Although the present invention has been described above in detail with reference to exemplary embodiments of the present invention, the scope of the present invention is not limited to specific embodiments, but should be construed based on the appended claims.

Further, it is understood by those skilled in the art that various modifications and changes can be made without departing from the scope of the present invention.

INDUSTRIAL APPLICABILITY

The gas sensor and the method of manufacturing the same according to the embodiment of the present invention may be used to sense various target gases including the hydrogen gas.

What is claimed is:

1. A method of manufacturing a gas sensor, the method comprising:
preparing a metal nanowire;
producing a thermoelectric composite by adding a polymer bead to the metal nanowire and then mechanically mixing the metal nanowire and the polymer bead;
producing a thermoelectric layer by hot-pressing the thermoelectric composite;
forming a first electrode on an upper surface of the thermoelectric layer and forming a second electrode on a lower surface of the thermoelectric layer; and
forming a heating catalyst layer on the first electrode,
wherein the heating catalyst layer includes Pd/Edge Oxidized Graphene (EOG) or Pt/EOG, and
wherein the Pd/EOG or the Pt/EOG is obtained by:
preparing an EOG dispersion solution by acid-treating graphite and then dispersing the graphite in an ionic liquid;
producing a Pd/EOG or Pt/EOG dispersion solution by adding a Pd precursor or a Pt precursor to the EOG dispersion solution and reducing the EOG dispersion solution including the Pd precursor or the Pt precursor; and
extracting the Pd/EOG or the Pt/EOG in the form of a paste from the Pd/EOG or Pt/EOG dispersion solution through centrifugation.

2. The method of claim 1, wherein the metal nanowire includes one or more materials selected from the group consisting of BixTey SbxTey, BixSey, SbxSey,(Bil-mSbm)xSey, PbSe, PbTe, CdSe, ZnSe, PbTeSe, (Bil-mSbm)xTey, CdTe, ZnTe, La3Te4, AgSbTe2, Ag2Te, AgPb18BiTe20, (GeTe)x(AgSbTe2)1-x (x is a real number smaller than 1), AgxPb18SbTe20 (x is a real number smaller than 1), AgxPb22.5SbTe20 (x is a real number smaller than 1), SbxTe20 (x is a real number smaller than 1), and BixSb2-xTe3 (x is a real number smaller than 2).

3. The method of claim 1, wherein
the preparing of the metal nanowire includes:
producing a base solution by adding a metal oxide to a solvent and then mechanically mixing the metal oxide and the solvent;
producing a source solution including the metal nanowire by adding a reducing agent to the base solution, and then mechanically mixing the reducing agent and the base solution; and
extracting the metal nanowire from the source solution through a washing and drying process.

4. The method of claim 1, wherein
in the producing the thermoelectric composite, a thermal treatment process is performed after the mechanical mixing, whereby the metal nanowire is adsorbed on a surface of the polymer bead due to a surface charge difference.

5. The method of claim 1, wherein
a Seebeck coefficient of the thermoelectric layer is adjusted depending on a content of the metal nanowire.

6. The method of claim 5, wherein
as the content of the metal nanowire increases, the Seebeck coefficient of the thermoelectric layer increases.

7. A gas sensor comprising:
a thermoelectric layer;
first and second electrodes that are spaced apart from each other with the thermoelectric layer interposed therebetween; and
a heating catalyst layer on the first electrode, wherein
the thermoelectric layer includes a structure compressed in a state in which metal nanowires are provided on a surface of a plurality of polymer beads,
wherein the heating catalyst layer includes Pd/EOG or Pt/EOG, and
wherein an EOG of Pd/EOG or Pt/EOG has selectively oxidized edges.

8. The gas sensor of claim 7, wherein
the metal nanowire includes one or more materials selected from the group consisting of BixTey SbxTey, BixSey, SbxSey,(Bil-mSbm)xSey, PbSe, PbTe, CdSe, ZnSe, PbTeSe, (Bil-mSbm)xTey, CdTe, ZnTe, La3Te4, AgSbTe2, Ag2Te, AgPb18BiTe20, (GeTe)x(AgSbTe2)1-x (x is a real number smaller than 1), AgxPb18SbTe20 (x is a real number smaller than 1), AgxPb22.5SbTe20 (x is a real number smaller than 1), SbxTe20 (x is a real number smaller than 1), and BixSb2-xTe3 (x is a real number smaller than 2).

9. A operation method of the gas sensor of claim 7, comprising:
generating a temperature difference in the thermoelectric layer by heat of reaction with a target gas and the heating catalyst layer; and
sensing a concentration of the target gas via an electromotive force generated by the temperature difference in the thermoelectric layer.

10. The gas sensor of claim 7, wherein the polymer beads include one or more materials selected from polymethylmethacrylate, polyamide, polypropylene, polyester, polyvinyl chloride, polycarbonate, polyphthalamide, polybutadiene terephthalate, polyethylene terephthalate, polyetylene, polyether ether ketone, and polystyrene.

\* \* \* \* \*